US012605248B2

(12) United States Patent
Freschauf et al.

(10) Patent No.: US 12,605,248 B2
(45) Date of Patent: Apr. 21, 2026

(54) DEVICE AND METHOD FOR TREATING VASCULAR INSUFFICIENCY

(71) Applicant: EDWARDS LIFESCIENCES CORPORATION, Irvine, CA (US)

(72) Inventors: Lauren R. Freschauf, Mission Viejo, CA (US); Ralph Schneider, Fallbrook, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 18/359,833

(22) Filed: Jul. 26, 2023

(65) Prior Publication Data

US 2023/0363910 A1     Nov. 16, 2023

Related U.S. Application Data

(63) Continuation of application No. 17/227,201, filed on Apr. 9, 2021, now Pat. No. 12,251,309, which is a
(Continued)

(51) Int. Cl.
| | |
|---|---|
| *A61F 2/24* | (2006.01) |
| *A61B 17/08* | (2006.01) |
(Continued)

(52) U.S. Cl.
CPC ............ *A61F 2/246* (2013.01); *A61B 17/083* (2013.01); *A61B 17/122* (2013.01);
(Continued)

(58) Field of Classification Search
CPC .............. A61B 17/083; A61B 17/1227; A61B 2017/00862; A61B 2017/00867;
(Continued)

(56) References Cited

U.S. PATENT DOCUMENTS

| | | | |
|---|---|---|---|
| 3,874,388 A | 4/1975 | King et al. | |
| 4,340,091 A | 7/1982 | Skelton et al. | |
(Continued)

FOREIGN PATENT DOCUMENTS

| | | |
|---|---|---|
| CN | 1142351 A | 2/1997 |
| CN | 106175845 A | 12/2016 |
(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Brigid K Byrd
(74) *Attorney, Agent, or Firm* — Anya Adams

(57) ABSTRACT

Embodiments of valve repair systems, leaflet clip devices, and methods of reducing regurgitation through a native heart valve are disclosed. A valve repair system can include a delivery apparatus and a leaflet clip device that is coupled to the delivery apparatus. The leaflet clip device can comprise an elongated clipping member, and a tensioning mechanism. One or more tensioning members are operatively connected to the tensioning mechanism to transform the clipping member from a delivery configuration to an implantation configuration. The one or more tensioning members can include a first tensioning member having a distal end portion that is connected to a first end portion of the clipping member and a second tensioning member having a distal end portion that is connected to a second end portion of the clipping member.

18 Claims, 10 Drawing Sheets

Related U.S. Application Data continuation of application No. 15/619,220, filed on Jun. 9, 2017, now Pat. No. 10,973,638.

(60) Provisional application No. 62/359,608, filed on Jul. 7, 2016.

(51) Int. Cl.
    *A61B 17/122*     (2006.01)
    *A61B 17/00*     (2006.01)

(52) U.S. Cl.
    CPC .... *A61B 17/1227* (2013.01); *A61B 2017/00243* (2013.01); *A61B 2017/00862* (2013.01); *A61B 2017/00867* (2013.01); *A61F 2210/0014* (2013.01); *A61F 2230/0045* (2013.01)

(58) Field of Classification Search
    CPC ......... A61B 17/122; A61B 2017/00243; A61F 2210/0014; A61F 2230/0045
    See application file for complete search history.

(56) References Cited

U.S. PATENT DOCUMENTS

| | | | |
|---|---|---|---|
| 4,506,669 A | 3/1985 | Blake, III | |
| 4,590,937 A | 5/1986 | Deniega | |
| 4,693,248 A | 9/1987 | Failla | |
| 4,803,983 A | 2/1989 | Siegel | |
| 5,125,895 A | 6/1992 | Buchbinder et al. | |
| 5,171,252 A | 12/1992 | Friedland | |
| 5,195,962 A | 3/1993 | Martin et al. | |
| 5,292,326 A | 3/1994 | Green et al. | |
| 5,327,905 A | 7/1994 | Avitall | |
| 5,363,861 A | 11/1994 | Edwards et al. | |
| 5,370,685 A | 12/1994 | Stevens | |
| 5,389,077 A | 2/1995 | Melinyshyn et al. | |
| 5,411,552 A | 5/1995 | Andersen et al. | |
| 5,450,860 A | 9/1995 | O'Connor | |
| 5,456,674 A | 10/1995 | Bos et al. | |
| 5,474,057 A | 12/1995 | Makower et al. | |
| 5,478,353 A | 12/1995 | Yoon | |
| 5,487,746 A | 1/1996 | Yu et al. | |
| 5,565,004 A | 10/1996 | Christoudias | |
| 5,607,462 A | 3/1997 | Imran | |
| 5,609,598 A | 3/1997 | Laufer et al. | |
| 5,611,794 A | 3/1997 | Sauer et al. | |
| 5,626,607 A | 5/1997 | Malecki et al. | |
| 5,695,504 A | 12/1997 | Gifford, III et al. | |
| 5,716,417 A | 2/1998 | Girard et al. | |
| 5,727,569 A | 3/1998 | Benetti et al. | |
| 5,741,297 A | 4/1998 | Simon | |
| 5,782,746 A | 7/1998 | Wright | |
| 5,797,960 A | 8/1998 | Stevens et al. | |
| 5,836,311 A | 11/1998 | Borst et al. | |
| 5,843,076 A | 12/1998 | Webster, Jr. et al. | |
| 5,855,590 A | 1/1999 | Malecki et al. | |
| 5,885,271 A | 3/1999 | Hamilton et al. | |
| 5,888,247 A | 3/1999 | Benetti | |
| 5,891,017 A | 4/1999 | Swindle et al. | |
| 5,891,112 A | 4/1999 | Samson | |
| 5,894,843 A | 4/1999 | Benetti et al. | |
| 5,921,979 A | 7/1999 | Kovac et al. | |
| 5,944,738 A | 8/1999 | Amplatz et al. | |
| 5,957,835 A | 9/1999 | Anderson et al. | |
| 5,972,020 A | 10/1999 | Carpentier et al. | |
| 5,980,534 A | 11/1999 | Gimpelson | |
| 6,004,329 A | 12/1999 | Myers et al. | |
| 6,010,531 A | 1/2000 | Donlon et al. | |
| 6,017,358 A | 1/2000 | Yoon et al. | |
| 6,086,600 A | 7/2000 | Kortenbach | |
| 6,120,496 A | 9/2000 | Whayne et al. | |
| 6,132,370 A | 10/2000 | Furnish et al. | |
| 6,162,239 A | 12/2000 | Manhes | |
| 6,165,183 A | 12/2000 | Kuehn et al. | |
| 6,182,664 B1 | 2/2001 | Cosgrove | |
| 6,193,732 B1 | 2/2001 | Frantzen et al. | |
| 6,193,734 B1 | 2/2001 | Bolduc et al. | |
| 6,200,315 B1 | 3/2001 | Gaiser et al. | |
| 6,228,032 B1 | 5/2001 | Eaton et al. | |
| 6,241,743 B1 | 6/2001 | Levin et al. | |
| 6,269,819 B1 | 8/2001 | Oz et al. | |
| 6,269,829 B1 | 8/2001 | Chen et al. | |
| 6,312,447 B1 | 11/2001 | Grimes | |
| 6,461,366 B1 | 10/2002 | Seguin | |
| 6,468,285 B1 | 10/2002 | Hsu et al. | |
| 6,508,806 B1 | 1/2003 | Hoste | |
| 6,508,825 B1 | 1/2003 | Selmon et al. | |
| 6,530,933 B1 | 3/2003 | Yeung et al. | |
| 6,537,290 B2 | 3/2003 | Adams et al. | |
| 6,544,215 B1 | 4/2003 | Bencini et al. | |
| 6,626,930 B1 | 9/2003 | Allen et al. | |
| 6,629,534 B1 | 10/2003 | St. Goar et al. | |
| 6,719,767 B1 | 4/2004 | Kimblad | |
| 6,764,510 B2 | 7/2004 | Vidlund et al. | |
| 6,770,083 B2 | 8/2004 | Seguin | |
| 6,837,867 B2 | 1/2005 | Kortelling | |
| 6,855,137 B2 | 2/2005 | Bon | |
| 6,913,614 B2 | 7/2005 | Marino et al. | |
| 6,926,730 B1 | 8/2005 | Nguyen et al. | |
| 6,939,337 B2 | 9/2005 | Parker et al. | |
| 6,945,956 B2 | 9/2005 | Waldhauser et al. | |
| 7,048,754 B2 | 5/2006 | Martin et al. | |
| 7,101,395 B2 | 9/2006 | Tremulis et al. | |
| 7,125,421 B2 | 10/2006 | Tremulis et al. | |
| 7,288,097 B2 | 10/2007 | Seguin | |
| 7,371,210 B2 | 5/2008 | Brock et al. | |
| 7,464,712 B2 | 12/2008 | Oz et al. | |
| 7,509,959 B2 | 3/2009 | Oz et al. | |
| 7,569,062 B1 * | 8/2009 | Kuehn | A61B 17/0643 |
| | | | 623/2.11 |
| 7,618,449 B2 | 11/2009 | Tremulis et al. | |
| 7,628,797 B2 | 12/2009 | Tieu et al. | |
| 7,682,369 B2 | 3/2010 | Seguin | |
| 7,731,706 B2 | 6/2010 | Potter | |
| 7,744,609 B2 | 6/2010 | Allen et al. | |
| 7,748,389 B2 | 7/2010 | Salahieh et al. | |
| 7,753,932 B2 | 7/2010 | Gingrich et al. | |
| 7,758,596 B2 | 7/2010 | Oz et al. | |
| 7,780,723 B2 | 8/2010 | Taylor | |
| 7,798,953 B1 * | 9/2010 | Wilk | A61B 17/0057 |
| | | | 600/16 |
| 7,803,185 B2 | 9/2010 | Gabbay | |
| 7,824,443 B2 | 11/2010 | Salahieh et al. | |
| 7,981,123 B2 | 7/2011 | Seguin | |
| 7,988,724 B2 | 8/2011 | Salahieh et al. | |
| 8,052,750 B2 | 11/2011 | Tuval et al. | |
| 8,070,805 B2 | 12/2011 | Vidlund et al. | |
| 8,096,985 B2 | 1/2012 | Legaspi et al. | |
| 8,104,149 B1 | 1/2012 | McGarity | |
| 8,133,239 B2 | 3/2012 | Oz et al. | |
| 8,133,241 B2 | 3/2012 | Boyd et al. | |
| 8,147,542 B2 | 4/2012 | Maisano et al. | |
| 8,172,856 B2 | 5/2012 | Eigler et al. | |
| 8,177,836 B2 | 5/2012 | Lee et al. | |
| 8,206,437 B2 | 6/2012 | Bonhoeffer et al. | |
| 8,216,301 B2 | 7/2012 | Bonhoeffer et al. | |
| 8,303,653 B2 | 11/2012 | Bonhoeffer et al. | |
| 8,313,525 B2 | 11/2012 | Tuval et al. | |
| 8,348,995 B2 | 1/2013 | Tuval et al. | |
| 8,348,996 B2 | 1/2013 | Tuval et al. | |
| 8,391,996 B2 | 3/2013 | Schaller | |
| 8,414,643 B2 | 4/2013 | Tuval et al. | |
| 8,425,404 B2 | 4/2013 | Wilson et al. | |
| 8,449,599 B2 | 5/2013 | Chau et al. | |
| 8,449,606 B2 | 5/2013 | Eliasen et al. | |
| 8,460,368 B2 | 6/2013 | Taylor et al. | |
| 8,470,028 B2 | 6/2013 | Thornton et al. | |
| 8,480,730 B2 | 7/2013 | Maurer et al. | |
| 8,540,767 B2 | 9/2013 | Zhang | |
| 8,579,965 B2 | 11/2013 | Bonhoeffer et al. | |
| 8,585,756 B2 | 11/2013 | Bonhoeffer et al. | |
| 8,647,254 B2 | 2/2014 | Callas et al. | |
| 8,652,202 B2 | 2/2014 | Alon et al. | |
| 8,668,733 B2 | 3/2014 | Haug et al. | |

(56) References Cited

U.S. PATENT DOCUMENTS

| | | | |
|---|---|---|---|
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 8,968,336 B2 | 3/2015 | Conklin et al. |
| 8,968,393 B2 | 3/2015 | Rothstein |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,537,348 B2 | 1/2020 | Rodriguez-Navarro et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0111641 A1 | 8/2002 | Peterson et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1* | 11/2004 | Greenhalgh ............ A61F 2/246 |
| | | 606/151 |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0085903 A1 | 4/2005 | Lau |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251177 A1 | 11/2005 | Saadat et al. |
| 2005/0251183 A1 | 11/2005 | Buckman et al. |
| 2005/0288786 A1 | 12/2005 | Chanduszko |
| 2006/0020275 A1* | 1/2006 | Goldfarb ............... A61B 17/08 |
| | | 606/151 |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281356 A1 | 11/2008 | Chau et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2009/0326567 A1 | 12/2009 | Goldfarb et al. |
| 2010/0022823 A1* | 1/2010 | Goldfarb ............ A61B 17/0401 |
| | | 600/37 |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0077668 A1 | 3/2011 | Gordon et al. |
| 2011/0082538 A1 | 4/2011 | Dahlgren et al. |
| 2011/0137410 A1 | 6/2011 | Hacohen |

(56)  References Cited

U.S. PATENT DOCUMENTS

| | | |
|---|---|---|
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0138121 A1 | 5/2013 | Allen et al. |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031864 A1 | 1/2014 | Jafari et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0222136 A1 | 8/2014 | Geist et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0257347 A1 | 9/2014 | Eidenschink |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0120642 A1 | 5/2016 | Shaolian et al. |
| 2016/0155987 A1 | 6/2016 | Yoo et al. |
| 2016/0157862 A1* | 6/2016 | Hernandez ......... A61B 17/1227 |
| | | 606/151 |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0071487 A1 | 3/2018 | Khuu et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126119 A1 | 5/2018 | McNiven et al. |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |

(56)  References Cited

U.S. PATENT DOCUMENTS

| | | |
|---|---|---|
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |
| 2024/0148505 A1 | 5/2024 | Datta et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| EP | 2739214 A2 | 6/2014 |
| FR | 2146050 A5 | 2/1973 |
| FR | 9711600 | 3/1997 |
| JP | 2010511469 A | 4/2010 |
| WO | WO-2005046453 A2 | 5/2005 |
| WO | 2014064694 A2 | 5/2014 |
| WO | 2016183485 A1 | 11/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

(56)                    References Cited

OTHER PUBLICATIONS

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi: 10.21037/jtd.2017.10.156, AME Publishing Company, Hong Kong, China.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et A., "Compassionate use of the PASCAL transcatheter mitral valve repair system for patients with severe mitral regurgitation: a multicentre, prospective, observational, first-in-man study," Lancet vol. 390, pp. 773-780, 2017.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003;14:841-853.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Umaña JP et al., "Bow-tie' mitral valve repair: an adjuvant technique for ischemic mitral regurgitation", Ann Thorac Surg., vol. 66, Issue—6, pp. 1640-1646, Nov. 1998.

Urban, Philip MD, "Coronary Artery Stenting", pp. 5-47, © 1991, ISBN: 2-88049-054-5, Editions Medecine et Hygiene, Geneva, Switzerland.

W. Xu et al., Shape Memory Alloy Fixator System for Suturing Tissue in Minimal Access Surgery, Annals of Biomedical Engineering, vol. 27, pp. 663-669, 1999.

W.M. Huang et al., "Shaping tissue with shape memory materials", Advanced Drug Delivery Reviews 65 (2013) pp. 515-535.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

* cited by examiner

DEVICE AND METHOD FOR TREATING VASCULAR INSUFFICIENCY

CROSS REFERENCE TO RELATED APPLICATION

This application is a continuation application of U.S. patent application Ser. No. 17/227,201, filed Apr. 9, 2021, which is a continuation application of U.S. patent application Ser. No. 15/619,220, filed Jun. 9, 2017, which claims the benefit of U.S. Provisional Patent Application No. 62/359,608, filed Jul. 7, 2016, each of which is incorporated herein by reference for all purposes.

FIELD

This disclosure relates to devices and methods of treating heart valve insufficiency.

BACKGROUND

Heart valve insufficiency typically involves regurgitation of blood through a heart valve that is unable to close completely or properly, resulting in impaired cardiovascular function. Valvular insufficiency can affect, for example, the mitral valve, the aortic valve, or the tricuspid valve, and can be associated with calcified or prolapsed leaflets, and/or expansion or deformation of the valve annulus. One method of treating heart valve insufficiency is to employ one or more leaflet clips to improve coaptation of the native valve leaflets. However, conventional leaflet clips can be difficult to implant, can interfere with the function of or damage associated valve structures such as chordae, and are frequently limited to use with a single type of heart valve. Accordingly, improvements to devices and methods of treating heart valve insufficiency are desirable.

SUMMARY

An exemplary embodiment of a leaflet clip device can comprise an elongated clipping member having a first end portion and a second end portion and a tensioning mechanism coupled to the clipping member. The leaflet clip device can further comprise one or more tensioning members disposed within a lumen of the clipping member, wherein the one or more tensioning members are operatively connected to the tensioning mechanism to transform the clipping member from a delivery configuration to an implantation configuration. Some embodiments of the clip device may further comprise a retaining mechanism disposed within the lumen of the clipping member, wherein the retaining mechanism retains the shape of the clipping member in the implantation configuration.

In some embodiments of the clip device, the clipping member can compromise a shape memory material. Additionally and/or alternatively, the tensioning mechanism can be centrally coupled to the clipping member with respect to the first end and the second end. In some embodiments, the one or more tensioning members can comprises a first tensioning member fixed at a distal end portion thereof to the first end portion of the clipping member and operatively connected to the tensioning mechanism at a proximal end portion of the first tensioning member, and a second tensioning member fixed at a distal end portion thereof to the second end portion of the clipping member and operatively connected to the tensioning mechanism at a proximal end portion of the second tensioning member. In some embodiments of the clip device, rotation of at least a portion of the tensioning mechanism can cause tensioning of the one or more tensioning members.

In some embodiments of the clip device, the implantation configuration can comprise a primary clipping region defined between two leg portions of the clipping member. Additionally and/or alternatively, the tensioning mechanism can comprise a retaining mechanism configured to retain the clipping member in the implantation configuration. Additionally and/or alternatively, the one or more tensioning members can extend through a portion of the tensioning mechanism. Additionally and/or alternatively, the one or more tensioning members are fixed at one end to a portion of the tensioning mechanism.

Additionally and/or alternatively, an exemplary leaflet clip device can comprise a clipping member comprising a tubular body having a lumen and two leg portions, wherein the clipping member can be transformed between a substantially linear delivery configuration and an implantation configuration in which the leg portions are drawn toward each other to capture a pair of leaflets between the leg portions and a tensioning mechanism configured to transform the clipping member from the delivery configuration to the implantation configuration. Additionally and/or alternatively, the clip device can further comprise one or more cords disposed within the lumen of the clipping member, wherein the one or more cords are operatively connected to the tensioning mechanism to transform the clipping member from the delivery configuration to the implantation configuration. Additionally and/or alternatively, rotation of at least a portion of the tensioning mechanism can cause tensioning of the one or more cords, which causes the clipping member to transform from the delivery configuration to the implantation configuration.

In some embodiments of the clip device, the tensioning mechanism can comprise a screw and a nut, the one or more cords being connected to the nut such that rotation of the screw causes the nut to move axially along the screw and apply tension to the one or more cords. In some embodiments the leaflet clip device can further comprise a retaining mechanism disposed within the lumen of the clipping member, wherein the retaining mechanism retains the clipping member in the implantation configuration.

Additionally and/or alternatively, the tubular body can comprise a metal tube having circumferential slots axially spaced along the length of the tubular body. Additionally and/or alternatively, the clipping member in the implantation configuration can have the shape of the Greek letter omega. Additionally and/or alternatively, when the clipping member is in the implantation configuration, the leg portions can extend toward each other from respective ends of an intermediate portion of the tubular body to define a clipping region for capturing the pair of leaflets, with the leg portions extending away from each other moving a direction away from the clipping region.

An exemplary method of reducing regurgitation through a native heart valve can comprise positioning a leaflet clip device adjacent the coaptation edges of two adjacent leaflets of the heart valve, wherein the leaflet clip device comprises a clipping member and first and second tensioning members disposed within a lumen of the clipping member, the first tensioning member fixed to a first end portion of the clipping member and the second tensioning member fixed to a second end portion of the clipping member, and applying tension to the tensioning members to transform the clipping member from a delivery configuration to an implantation configuration in which the coaptation edges of the leaflets are captured between two leg portions of the clipping member.

Additionally and/or alternatively, applying tension can include rotating a tensioning mechanism operatively coupled to the first and second tensioning members. In some embodiments the method can comprise engaging a retaining mechanism to retain the clipping member in the implantation configuration. Additionally and/or alternatively, the clipping member can have a substantially linear shape in the delivery configuration.

The foregoing and other objects, features, and advantages of the invention will become more apparent from the following detailed description, which proceeds with reference to the accompanying figures.

DETAILED DESCRIPTION

Figures 1, 2:
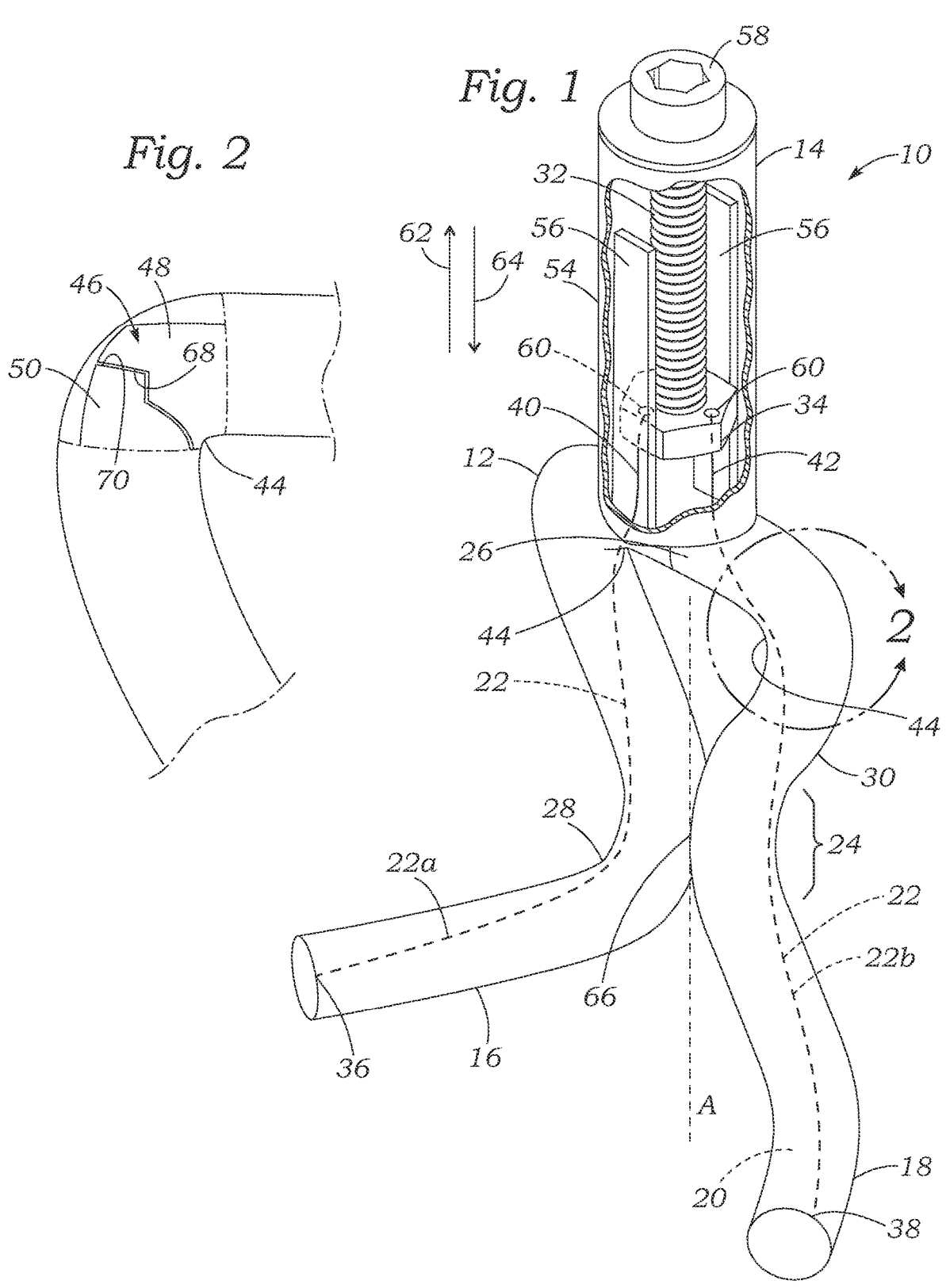
FIG. 1 is a perspective view of a representative embodiment of a leaflet clip device with a portion of a tensioning mechanism broken away for purposes of illustration.
FIG. 2 is enlarged portion of a clipping member of the clip device of FIG. 1, shown partially broken away for purposes of illustration.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example are to be understood to be applicable to any other aspect, embodiment or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The invention is not restricted to the details of any disclosed embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures cannot show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

FIG. 1 illustrates a representative embodiment of a leaflet clip device 10. The clip device 10 in the illustrated embodiments comprises an elongate clipping member 12 and a tensioning mechanism 14. The clipping member 12 can comprise an elongate generally tubular or cylindrical body having a first end portion 16, a second end portion 18, a lumen 20 extending from the first end portion 16 to the second end portion 18. The tensioning mechanism 14 can comprise one or more cords or tensioning members 22 disposed within the lumen 20 of the clipping member 12. As used herein, the term "tensioning member" or "cord" refers to a slender length of material that can be formed from a single wire, strand, fiber, or filament, or can comprise multiple wires, strands, fibers, or filaments.

The clipping member 12 can be transformed from a delivery configuration to an implantation configuration, and vice versa. In the delivery configuration, the clipping member 12 can be in a substantially longitudinally extended or straightened configuration (see FIG. 7). In the implantation configuration (see FIG. 1), two portions of the clipping member 12 are drawn toward each other forming a primary clipping region 24, such that a portion of one or more native valve leaflets can be captured, or pinched, between the two portions of the clipping member within the primary clipping region (see FIG. 6).

The clipping member 12 in the illustrated embodiment has a shape similar to the Greek letter "omega" in the implanted configuration. In particular, the clipping member 12 can have an intermediate portion 26 (which can extend linearly as shown or can be curved) and first and second leg portions 28, 30, respectively, which extend toward each other moving in a direction extending away from respective ends of the intermediate portion 26 to form the clipping region 24. The leg portions 28, 30 then extend away from each other moving in a direction extending away from the clipping region 24. Other delivery configurations for the clipping member 12 are also possible. For example, the clipping member 12 can be folded in half such that the first and second leg portions 28, 30 are straightened and extend parallel and side-to-side with respect to each other in the delivery configuration.

Figures 5, 6:
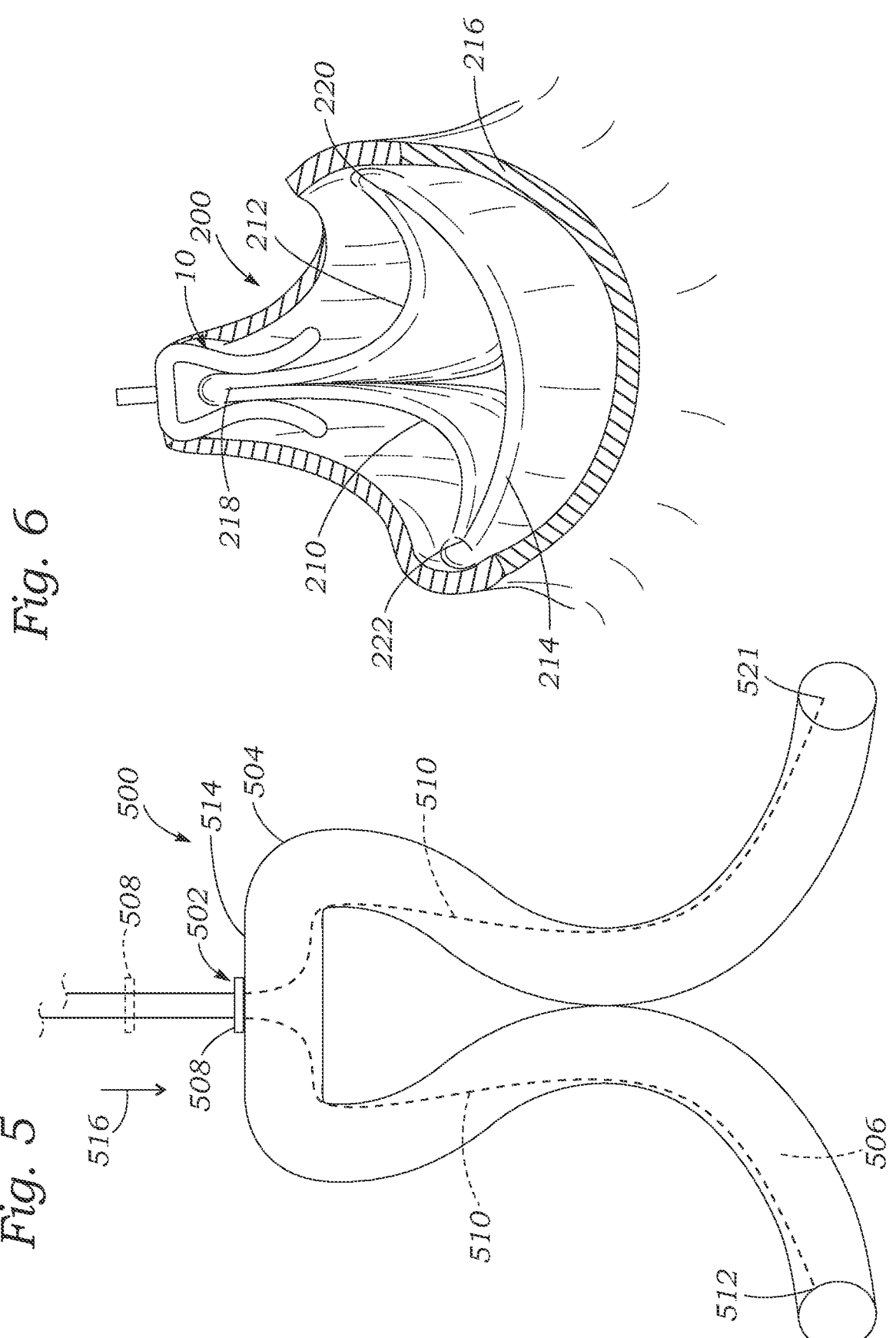
FIG. 5 is a front elevation view of another representative embodiment of a leaflet clip device.
FIG. 6 is a perspective view of a representative embodiment of a leaflet clip device implanted in the native aortic valve.

The leaflet clip device 10, and any of the other leaflet clip embodiments described herein, can be used to treat valvular insufficiency or regurgitation by remodeling the annulus and/or the leaflets of a heart valve. For example, FIG. 6 illustrates a leaflet clip device 10 situated in a native aortic valve 200. The native aortic valve 200 can include three valve leaflets 210, 212, 214 attached to a valve annulus 216. The valve leaflets 210 and 212 can form a first commissure 218, the leaflets 212 and 214 can form a second commissure 220, and the leaflets 210 and 214 can form a third commissure 222.

The leaflet clip device 10 is shown situated adjacent the first commissure 218, such that the leaflet clip device 10 engages the leaflets 210 and 212. The leaflet clip device 10 is also shown situated near the wall of the valve annulus 216. In this manner, the leaflet clip 10 can improve coaptation of the leaflets 210, 212 at the commissure 218, thereby reducing regurgitation through the valve 200 due to valvular insufficiency. Additionally, although the leaflet clip 10 is shown clipped to the respective valve leaflets adjacent the annulus 216, the leaflet clip 10 can be clipped to the valve leaflets at any suitable location along the leaflets, including at the center of the native valve, as desired.

Although one clip device 10 is shown implanted in the native aortic valve, a plurality of leaflet clips 10 can be implanted to reduce dilatation of the annulus 216 and/or to address abnormalities in the shape of the annulus 216. For example, a leaflet clip 10 can be implanted on each pair of leaflets, for example, at each commissure 218, 220, 222.

Alternatively or additionally, multiple clip devices 10 can be implanted along the coaptation edges of a pair of adjacent leaflets. For example, multiple clip devices 10 can be implanted along the coaptation edges of leaflets 210, 212.

Referring again to FIG. 1, the tensioning mechanism 14 can be operatively coupled to the clipping member 12 via the tensioning members 22, which apply tension to the clipping member 12 to transform the clipping member 12 from the delivery configuration to the implantation configuration and/or to bring the leg portions 28, 30 closer together to the final implantation configuration after partial deployment from the delivery configuration, as further described below.

Figure 13:
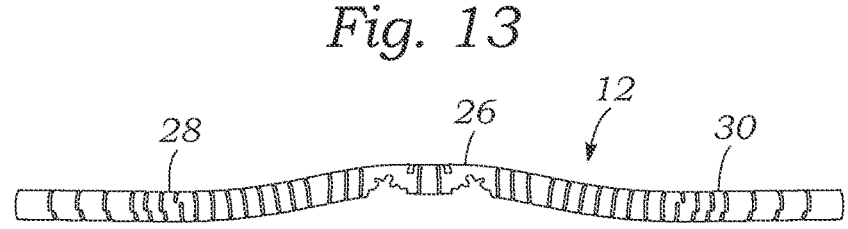
FIG. 13 is a front view of a clipping member formed from a laser cut metal tube, according to one embodiment.
Figure 16:
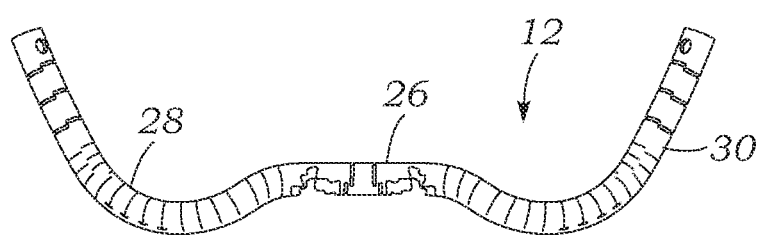
FIG. 16 is a front view of a clipping member formed from a laser cut metal tube, according to another embodiment.

In particular embodiments of the leaflet clip device 10, the clipping member 12 can be formed (e.g., laser cut) from a metal tube, such as shown in FIGS. 13 and 16. The tube can be formed with a plurality of slots or cuts along the length of the tube to promote bending of the tube from the delivery configuration to the implantation configuration.

In some embodiments, the clipping member 12 can be formed from a nonlinearly elastic, super-elastic, and/or shape-memory material, such as Nitinol, and is shape set in the implantation configuration. The clipping member 12 can be retained in the delivery configuration during delivery of the device within a patient's body, such as with a sheath of a delivery apparatus, and when released from the delivery configuration, the clipping member 12 automatically reverts back toward the implantation configuration. In some embodiments, the clipping member 12 can self-deploy under its own resiliency from the delivery configuration to a partially deployed configuration such that the leg portions 28, 30 are spaced apart from each other at the clipping region 24. The tensioning mechanism 14 can then be used to draw the leg portions 28, 30 closer together to the implantation configuration shown in FIG. 1 with sufficient force to engage and anchor itself onto a pair of native valve leaflets. In other embodiments, the clipping member can be shape set in a substantially straight or linear deliver configuration and the tensioning mechanism 14 is used to deform or bend the clipping member from the delivery configuration to the implantation configuration.

In alternative embodiments, the clip device 10 does not have a tensioning mechanism 14 and the shape-memory material of the clipping member 12 causes the clipping member 12 to transform from the delivery configuration to the implantation configuration under its own resiliency and provide sufficient force against the native leaflets to anchor the clipping member 12 onto a pair of the native leaflets without a separate tensioning mechanism.

In other embodiments, the clipping member 12 can be formed from a linearly elastic material, such as stainless steel or cobalt chromium alloy. In such embodiments, the tensioning mechanism 14 can be used to transform or deform the clipping member 12 from the delivery configuration to the implantation configuration. Linearly elastic metals, such as stainless steel or cobalt chromium alloy, also deform plastically after an applied force exceeds a predetermined threshold. In some embodiments, the tensioning mechanism 14 can be used to plastically deform the clipping member 12 as it is deformed from the delivery configuration to the implantation configuration.

Figure 14:
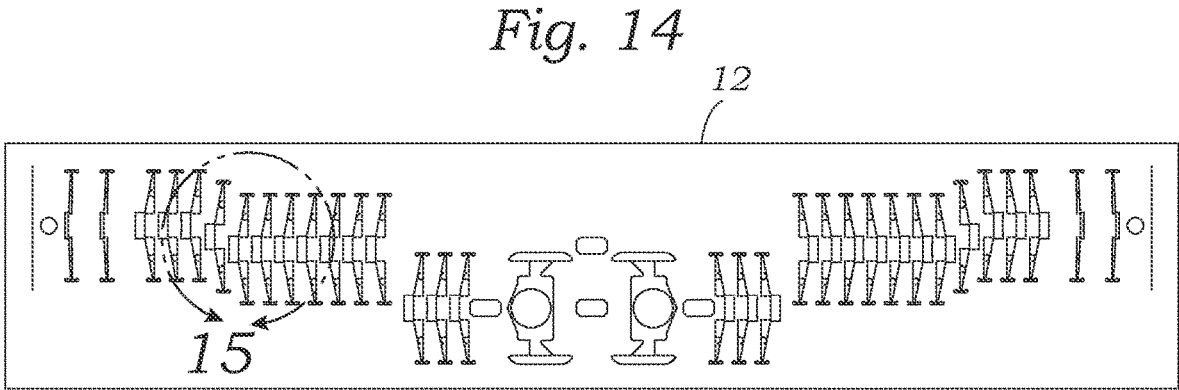
FIG. 14 illustrates a cut pattern for laser cutting a metal tube to form a clipping member, such as shown in FIG. 13.
Figure 15:
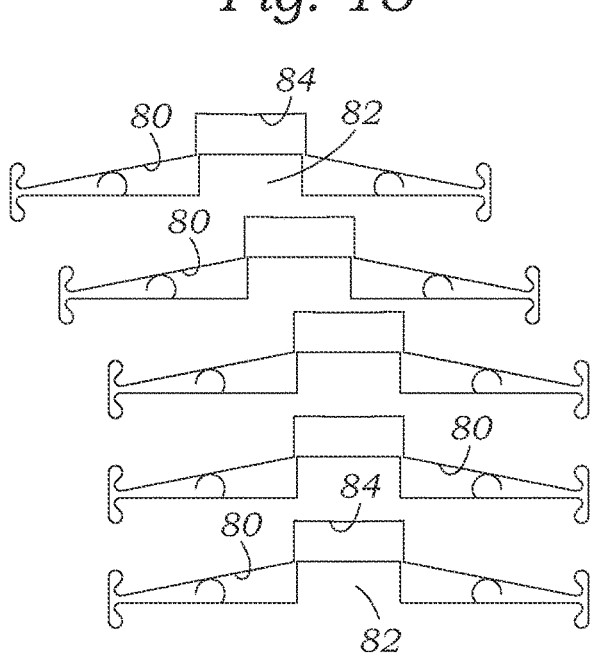
FIG. 15 is an enlarged view of a portion of the cut pattern shown in FIG. 14.

FIG. 13 illustrates an example of a clipping member 12 formed from a laser cut metal tube. FIG. 14 shows an exemplary cut pattern for the metal tube used to form the clipping member 12 shown in FIG. 13. FIG. 15 is an enlarged view of a portion of the cut pattern shown in FIG. 14. Although not shown, the clipping member can include a covering extending over and covering the outer surface of the metal tube. The covering can comprise a suitable fabric (e.g., a polyethylene terephthalate (PET) fabric), non-fabric polymeric materials (e.g., polyurethane or silicone), or natural tissue (e.g., pericardium tissue)

As shown in FIGS. 14 and 15, a series of axially-spaced, circumferential cuts can be formed in the clipping member 12 at selected locations. Along the leg portions 28, 30, the cuts form a series of circumferential gaps 80 with tabs 82 and notches 84 on opposite sides of central portions of the gaps 80. In the illustrated embodiment, the clipping member 12 has no or substantially no shape memory toward the implantation configuration and is shown in FIG. 13 in its natural resting state prior to being transformed into the implantation configuration. The clipping member in this example can comprise, for example, a stainless steel or cobalt chromium alloy metal tube. By application of forces to the clipping member 12, as further described below, it can be transformed from a substantially straight or linear configuration to the implantation configuration shown in FIG. 1. The gaps 80 promote bending of the clipping member as it is bent into the implantation configuration. The tabs 82 can reside in corresponding notches 84 to resist undesirable torqueing of the clipping member as it is transformed into the implantation configuration.

Figure 17:
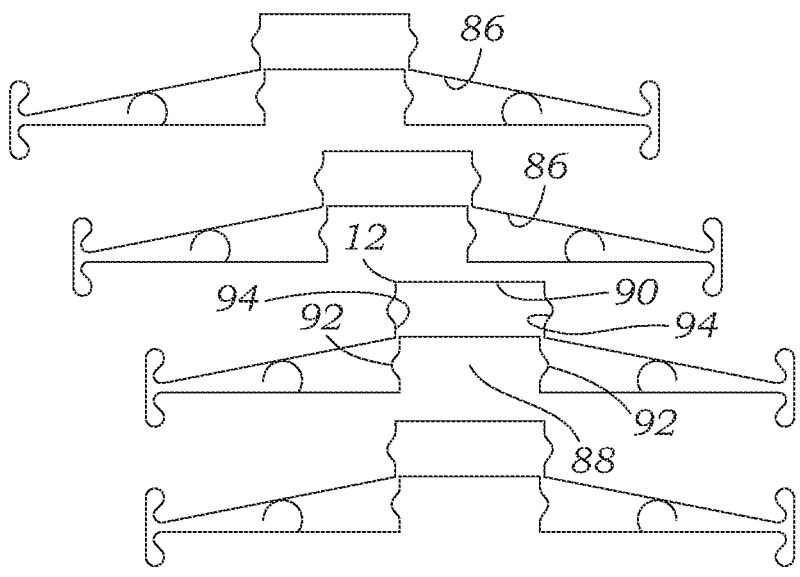
FIG. 17 is an enlarged view of a portion of a cut pattern for laser cutting a metal tube to form a clipping member, such as shown in FIG. 16.

FIG. 16 shows another example of a clipping member 12 formed from a laser cut metal tube. The clipping member 12 of FIG. 16 can be substantially the same as the clipping member of FIG. 13 except that the circumferential cuts form mating features that help maintain the shape of the clipping member when being transformed into the implantation configuration. In particular, as shown in FIG. 17, the cuts form a series of circumferential gaps 86 with tabs 88 and notches 90 on opposite sides of central portions of the gaps 86. The tabs 88 have non-linear opposing edges 92 that can engage similarly shaped non-linear edges 94 of the notches 90 when the clipping member is bent toward the implantation configuration. The edges 92 of the tabs 88 can frictionally engage the edges 94 of the notches 90 to resist straightening of the clipping member back toward the delivery configuration. FIG. 16 shows the clipping member retained in a partially deployed state by the retaining features of the cuts without application of other forces on the clipping member. In some embodiments, the retaining features of the cuts can be configured to retain the shape of the clipping member in the implantation configuration shown in FIG. 1.

When the clipping member 12 is in the implanted configuration, the clipping strength of the leaflet clip device can be determined. As used herein, the terms "clip retention force" and "clipping strength" refer to a force in the proximal direction that can be withstood by a leaflet clip device without disengaging from the leaflets of a heart valve when the clipping member is in the implantation configuration. In some embodiments, the clip device and/or a delivery apparatus for the clip device can include a strain gauge or equivalent device that is operable to measure the retention force of the leaflet clip device 10.

The tensioning mechanism 14 can be configured to permit fine closure movement of the leaflet clip device to the implantation configuration. In particular embodiments, the clip retention force can be completely controllable via the tensioning mechanism 14. For example, in the embodiment illustrated in FIGS. 1 and 3, the tensioning mechanism 14 can comprise a screw 32 and a moveable element such as a nut 34, which is threadably engaged with and moveable along the length of the screw 32. The tensioning mechanism 14 can further include a housing 54 containing the screw 32 and the nut 34, and two plates or bars 56 on opposite sides of the nut 34. The plates 56 contact adjacent surfaces of the nut 34 and prevent rotation of the nut 34 upon rotation of the screw 32. Hence, rotation of the screw 32 produces axial movement of the nut 34 along the length of the screw within the housing 54.

The screw 32 can have a proximal end portion 58 that can be releasably connected to a delivery apparatus or another tool that can be manipulated to rotate the screw 32. For example, a rotatable shaft of a delivery apparatus or another tool can have a distal end portion releasable connected to the proximal end portion 58 of the screw 32. The proximal end portion of the shaft can be rotated by a user (either manually or by activating a motor that rotates the shaft), which in turn rotates the screw 32.

A first cord 22a can have a distal end portion 36 attached to the first end portion 16 of the clipping member 12 and a second cord 22b can have a distal end portion 38 attached to the second end portion 18 of the clipping member 12. The distal end portions 36, 38 of the cords 22a, 22b can be fixedly secured to portions of the clipping member 12, such as by welding the distal end portions 36, 38 to the luminal surface of the clipping member 12. Proximal end portions 40, 42 of the first and second cords 22a, 22b can be fixedly secured to the nut 34, for example, by placing the proximal end portions 40, 42 into respective bores 60 in the nut 34 and welding them into place. Tension can be applied to the first and second cords 22a, 22b by movement of the nut 34 away from the clipping member 12 along the length of the screw 32 in the proximal direction, as indicated by arrow 62. Tension on the first and second cords 22a, 22b can be released or eased by movement of the nut 34 towards the clipping member 12 in the distal direction, as indicated by arrow 64.

Tensioning of the cords 22a, 22b is effective to apply a compressive or buckling force to the leg portions 28, 30, which causes the leg portions to buckle at the clipping region 24 and/or cause the leg portions to be drawn closer together at the clipping region and apply sufficient retention force against the native leaflets along the coaptation edges of the leaflets. Further tensioning of the cords 22a, 22b can permit manipulation of the intermediate portion 26 of the clipping member to perform reshaping of the cusp region of the native valve. As noted above, the clipping member 12 can be comprised of flex cuts and/or thinning of tube material at predetermined locations along the clipping member 12 where bending of the clipping member 12 is desired, for example thinning and/or flex cuts at bends 44, 66. The length, positioning, frequency, and amount of material removal of the flex cuts can allow for a multitude of options to produce flexion in specific areas in a defined sequence, location, resolution, and with a defined curvature.

Fine closure movement of the leaflet clip device 10 can depend on the pitch of threading of the screw 32. For example, a relatively smaller pitch will increase the amount of control over the spacing between the leg portions 28, 30 at the clipping region 24 and the retention force applied to a pair of native leaflets.

In lieu of or in addition to locking flex cuts (as shown in FIG. 17), some embodiments of the leaflet clip device 10 can include one or more retaining features to help retain the clipping member 12 in its implantation configuration. For example, the clipping member 12 can comprise a retaining mechanism 46 at each bend 44, which retains that portion of the clipping member in its deformed state once a predetermined angle of curvature in the clipping member 12 is reached. As shown in FIG. 2, each locking mechanism 46 can be disposed within the lumen of the clipping member 12 at bends 44. Each locking mechanism 46 can include at least a first locking member 48 and a second locking member 50 configured to move relative to each other as the clipping member is transformed from the delivery configuration to the implantation configuration. The locking members 48, 50 can have opposing edges having complimentary shapes that nest against each other in the implantation configuration. For example, the first locking member 48 can have a notch 68 that receives a projection 70 of the second locking member 50.

When the clipping member 12 is substantially straightened in the delivery configuration, the locking members 48, 50 are placed in an overlapping position relative to each and can slide against one another as the clipping member 12 moves toward the implantation configuration. When the bend 44 reaches a predetermined curvature, for example when the implantation configuration is reached, and the projection 70 moves into engagement within the notch 68, as shown in FIG. 2. The locking members 48, 50 can be biased laterally against each other to force the projection 70 to engage the notch 68. Engagement of the locking members 48, 50 resists further bending of the clipping member at bend 44 beyond the implantation configuration and bending of the clipping member back toward the delivery configuration at bend 44. The retaining members 46 can decrease the load placed on the cords 22a, 22b and can increase the ability of the clip device to maintain a consistent retention force on the leaflets for a longer period of time.

Additionally and/or alternative, the tensioning mechanism 14 can also include a retaining or locking mechanism for retaining the clipping member 12 in the implantation configuration. For example, the tensioning mechanism 14 can retain the clipping member in the implantation configuration due to the balance of tension forces in the one or more cords 22 with the frictional forces between the screw 32 and the nut 34. In this manner, the screw 32 and the nut 34 serve as a retaining mechanism. Additionally and/or alternatively, a variable pitch screw can provide a retaining mechanism whereby a nut 34 can travel along a first portion of the screw having a first pitch and then locks onto or creates a mechanical interference with a second portion of the screw having a second pitch different than the first pitch, as further described below in connection with FIGS. 9-10.

Figure 7:
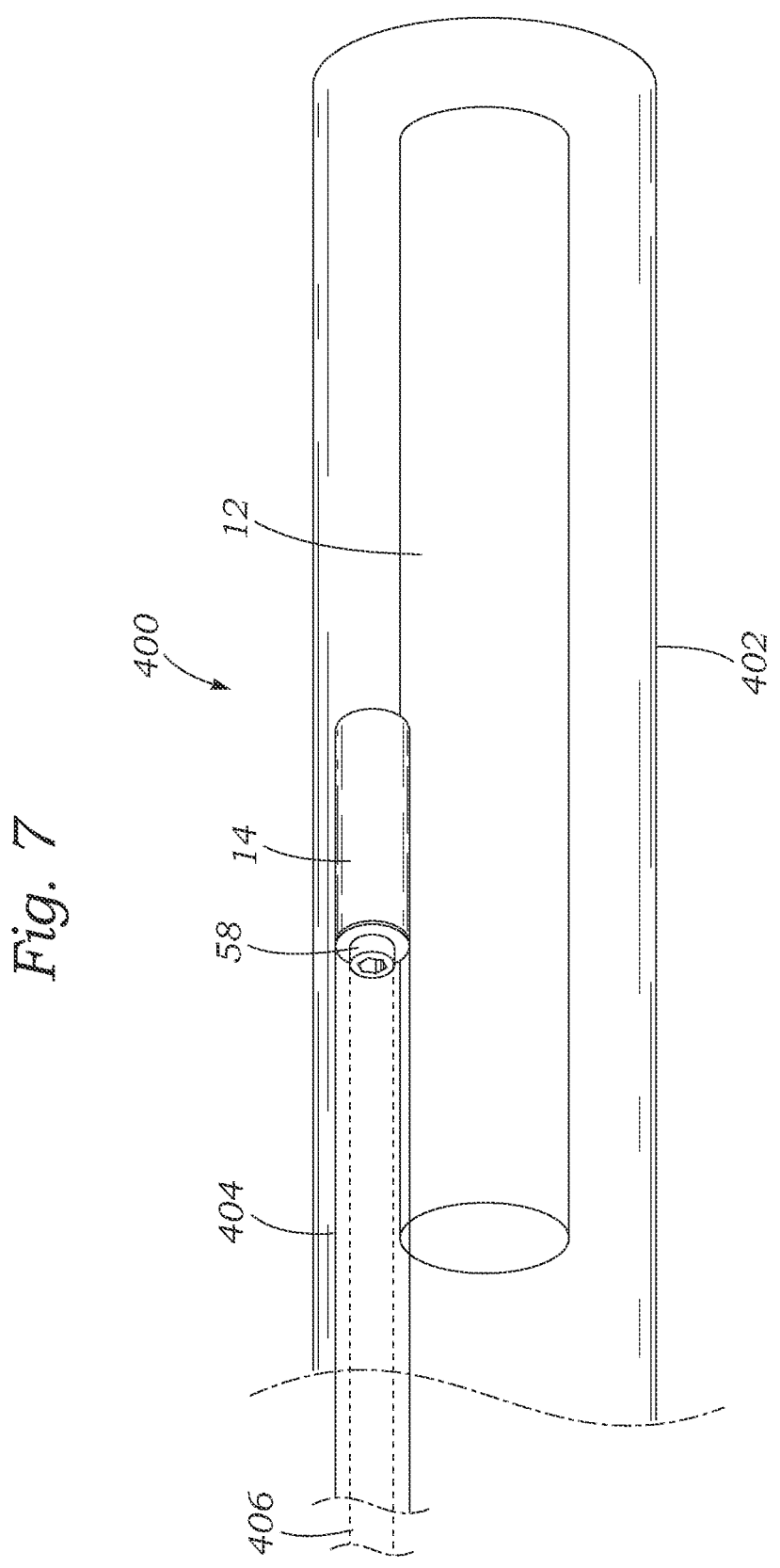
FIG. 7 is a side view of a delivery apparatus and leaflet clip device loaded in the delivery apparatus for delivery into a patient's body.

FIG. 7 shows the distal end portion of a delivery apparatus 400 for delivering and implanting a clip device 10 percutaneously within a patient's body, according to one embodiment. The delivery apparatus can comprise an outer sheath 402, a first shaft 404 extending through the sheath 402, and a second shaft 406 extending through the first shaft 404. The sheath 402 has a lumen sized to receive and retain the clip device 10 in the delivery configuration for delivery through the patient's body. The inner shaft 404 can be releasably connected to a convenient location on the clip device, as the tensioning mechanism 14 as shown. The shaft 404 can be used to manipulate or adjust the position of the clip device 10 relative to the sheath 402 and the implantation location. For example, the shaft 404 can be used to deploy the clip device 10 from the sheath 402, move the clip device distally and proximally relative to the implantation location, and/or rotate the clip device relative to the implantation location. The second shaft 406 can be releasably coupled to the proximal end portion 58 of the screw 32 of the tensioning mechanism 14. The second shaft 406 can be rotated relative to the first shaft 404 by a user to rotate the screw 32 and adjust the tension on the cords 22a, 22b. The proximal end portions of the sheath 402, the first shaft 404, and the second shaft 406 can be coupled to a handle of the delivery apparatus, which can include appropriate controls (e.g., knobs) that allow a user to control movement the sheath 402, the first shaft 404, and the second shaft 406.

The delivery apparatus 400 and a clip device 10 contained within the sheath 402 can be introduced into a patient's vasculature (e.g., via the femoral artery or other suitable access point) and percutaneously advanced to the patient's heart with a leaflet clip device 402 using any of various delivery techniques. In a transfemoral procedure, the delivery apparatus 400 can be inserted through a femoral artery and the aorta to the heart in a retrograde direction (typically, but not exclusively used for deploying a clip on the leaflets of the aortic or mitral valves). Similarly, the delivery apparatus 400 can be inserted through a femoral vein and the vena cava to the right side of the heart in an antegrade direction (typically, but not exclusively used for deploying a clip on the leaflets of the pulmonary or tricuspid valves). In a transventricular procedure, the delivery apparatus 400 can be inserted through a surgical incision made in the chest and on the bare spot on the lower anterior ventricle wall (typically, but not exclusively used for deploying a clip on the leaflets of the aortic or mitral valves). Similarly, the delivery apparatus 400 can be inserted through a surgical incision on the wall of the right ventricle to access the pulmonary or tricuspid valves. In a transatrial procedure, the delivery apparatus 400 can be inserted through a surgical incision made in the wall of the left or right atrium to access the native valves on the left or right sides, respectively, of the heart. In a transaortic procedure, the delivery apparatus 400 can be inserted through a surgical incision made in the ascending aorta and advanced toward the heart (typically, but not exclusively used deploying a clip on the leaflets of the aortic or mitral valves). In a transseptal procedure, the delivery apparatus 400 can be advanced to the right atrium, such as via a femoral vein, and through the septum separating the right and left ventricles (typically, but not exclusively used for deploying a clip on the leaflets of the aortic or mitral valves). Further details of delivery techniques for accessing the native valves of the heart are disclosed in U.S. Patent Publication No. 2014/0067052, which is incorporated herein by reference.

Once located proximate the desired heart valve, the leaflet clip device 10 can then be deployed from the sheath 402, such as by pushing the clip device 10 distally from the sheath 402 using the shaft 404 and/or retracting the sheath 402 relative to the clip device. Once the clip device is deployed from the sheath, the clip device can be advanced distally, retracted proximally, and/or rotated as needed to position the leaflet clip device 10 such that a pair of first and second leaflets are positioned generally within the primary clipping region 24 with the first leg portion 28 adjacent one of the leaflets and the second leg portion 30 adjacent the other leaflet.

The delivery apparatus can be used to adjust the tensioning mechanism 14 until the desired predetermined implantation configuration is achieved with the leaflets engaged and pinched between the leg portions 28, 30. For example, the user can rotate the shaft 406, which rotates the screw 32, thereby increasing tension on the cords 22a, 22b until the implantation configuration is achieved.

Figures 3, 4:
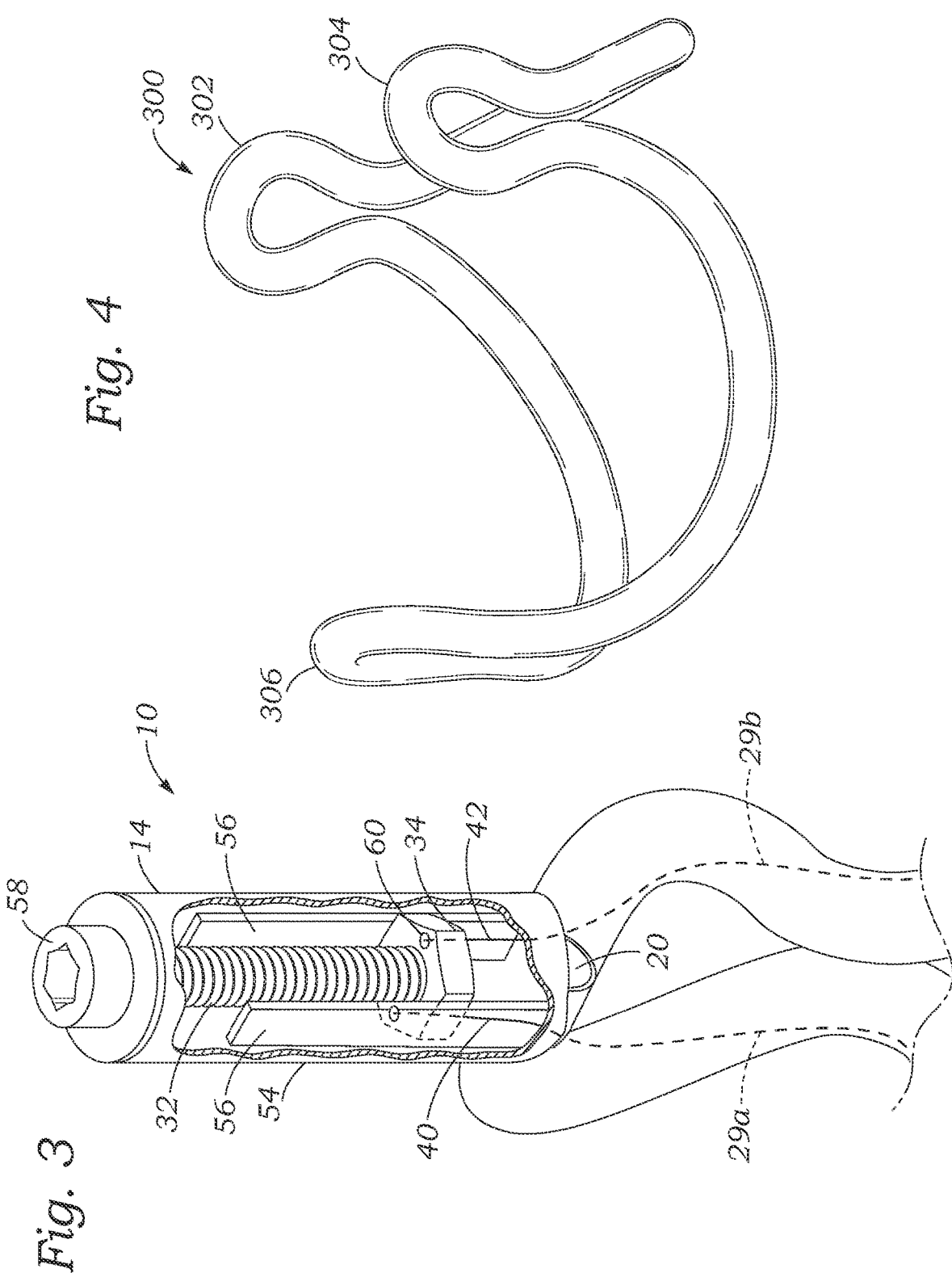
FIG. 3 is an enlarged portion of the leaflet clip device of FIG. 1, shown partially broken away for purposes of illustration.
FIG. 4 is a perspective view of another representative embodiment of a leaflet clip device having a plurality of integral clipping members for engaging multiple pairs of leaflets.

In alternative embodiments, a clip device can comprise multiple clipping members that are configured to engage multiple pairs of native leaflets. As shown in FIG. 4, for example, a leaflet clip device 300 comprises an annular ring having three clipping members 302, 304, 306 spaced approximately 120 degrees from each other, each configured to be implanted on a pair of native leaflets, such as at a commissure of the native valve. The clip device 300 can comprise a tubular structure and be formed from, for example, a shape-memory material (e.g., Nitinol) or a plastically-deformable material (e.g., stainless steel or cobalt chromium alloy). In other embodiments, the clip device can comprise an annular ring having two clipping members spaced approximately 180 degrees from each other, such as for implantation on the leaflets of the native mitral valve.

In still alternative embodiments, the clip device can comprise an open ring (i.e., a ring that extends less than 360 degrees) having a number of clipping members that is less than the number of native leaflets of the valve in which the device is to be implanted. For example, the clip device can comprise an open ring having two clipping members spaced approximately 120 degrees from each other and is configured to engage two pairs of native leaflets but not the third pair of native leaflets.

A leaflet clip device can include any one of a number of different tensioning mechanisms configured to apply tension to one or more cords disposed within a clipping member and/or transform the clipping member from a delivery configuration to an implantation configuration. For example, FIGS. 5 and 8-12 illustrate various embodiments of a leaflet clip device having different tensioning mechanisms.

FIG. 5 illustrates a leaflet clip device 500, according to another embodiment. The leaflet clip 500 comprises a tensioning mechanism 502 and a clipping member 504 defining a lumen 506. The tensioning mechanism 502 can comprise one or more fasteners 508. One or more cords 510 can be disposed within the lumen 506 and can be attached at their distal end portions 512 to respective locations on the clipping member 504, as described above in connection with the embodiment of FIG. 1. The one or more cords 510 can pass through the fastener 508 and can have proximal end portions connected to a delivery apparatus and/or extending outside of the patient's body. The fastener 508 (such as a suture clip) can be advanced over the cords 510 in the direction indicated by arrow 516 and pushed against an intermediate portion 514 of the clipping member 504 so as to retain tension on the cords. The portions of the cords proximal to the clipping member 504 can be severed with the delivery apparatus or another tool.

The fastener 508 can be a suture clip, or another type of fastener that can be deployed from a catheter and secured to a suture within the patient's body. Various suture clips and deployment techniques for suture clips that can be used in the methods disclosed in the present application are disclosed in U.S. Publication Nos. 2014/0031864 and 2008/0281356 and U.S. Pat. No. 7,628,797, which are incorporated herein by reference. In the case of a slideable fastener, the fastener 508 can be movable along the cords 510 in a distal direction toward the clipping member, and configured to resist movement in a proximal direction along the cords in the opposite direction. Thus, once placed against the clipping member, the fastener 508 can resist the cords 510 pulling through the fastener under the tension of the cords. In this manner, the fastener 508 serves as a retaining member to assist in maintaining the shape of the clipping member in the implantation configuration.

The delivery apparatus can include a mechanism configured to adjust the tension applied to the cords 510 until the desired predetermined implantation configuration is achieved. For example, the cords 510 can be releasably coupled to respective shafts or other components that can be controlled by a user. The delivery apparatus can also include a mechanism for deploying the fastener 508 onto the cords and/or advancing the fastener 508 over the cord until it abuts the clipping member.

Figure 8:
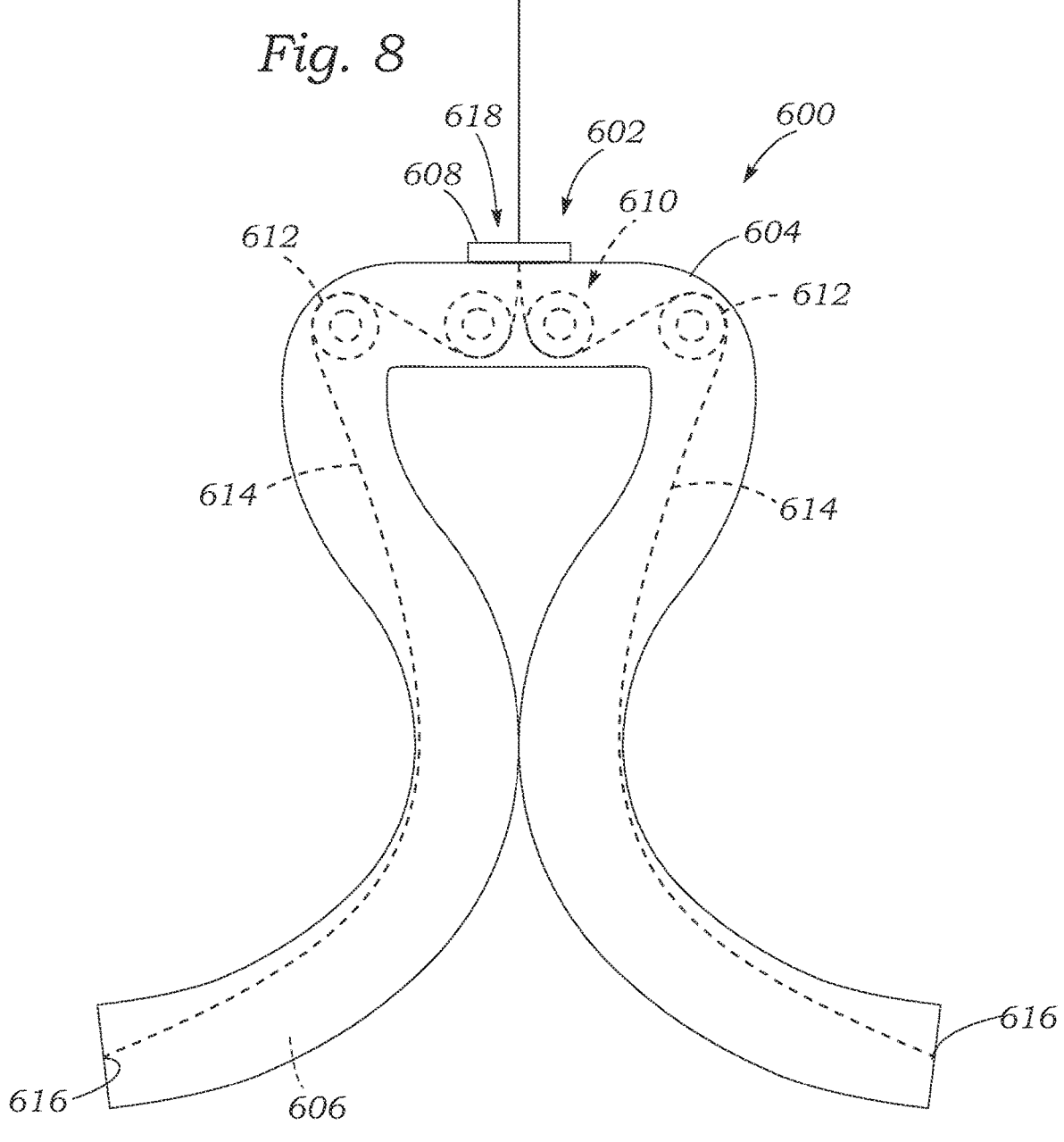
FIG. 8 is a front elevation view of another representative embodiment of a leaflet clip device.

FIG. 8 illustrates a leaflet clip device 600, according to another embodiment. The clip device 600 comprises a tensioning mechanism 602 and a clipping member 604 defining a lumen 606. The tensioning mechanism 602 can comprise one or more fasteners 608 (e.g., suture clips) and a pulley system 610 comprising one or more pulley wheels or sheaves 612 disposed within the lumen 606. One or more cords 614 can be disposed within the lumen 606 and attached at their distal end portions 616 to respective locations on the clipping member 604, as described above in connection with the embodiment of FIG. 1. The one or more cords 614 can pass through the fastener 608 that allows for one directional movement of the cords 614 through the fastener. As shown, the cords 614 can be weaved around the wheels 612 as they extend through the lumen.

The delivery apparatus can include a mechanism that allows tension to be applied to the cords 614 within the clipping member 604 until the desired predetermined implantation configuration is achieved and a mechanism to deploy and advance the fastener 608 over the cords 614, as discussed above in connection with the embodiment of FIG. 5. The use of pulley wheels 612 to support the cords 614 in advantageous in that it significantly reduces the force required to deform the clipping member to the implantation configuration by application of tensile forces on the cords. The pulley wheels 612 are also positioned at strategic locations within the lumen to promote flexing of the clipping member at the desired locations upon application of tension on the cords. Other uses of a pulley system could further distribute the tension force/load on the cords depending upon the needs of the procedure.

Figures 9, 10:
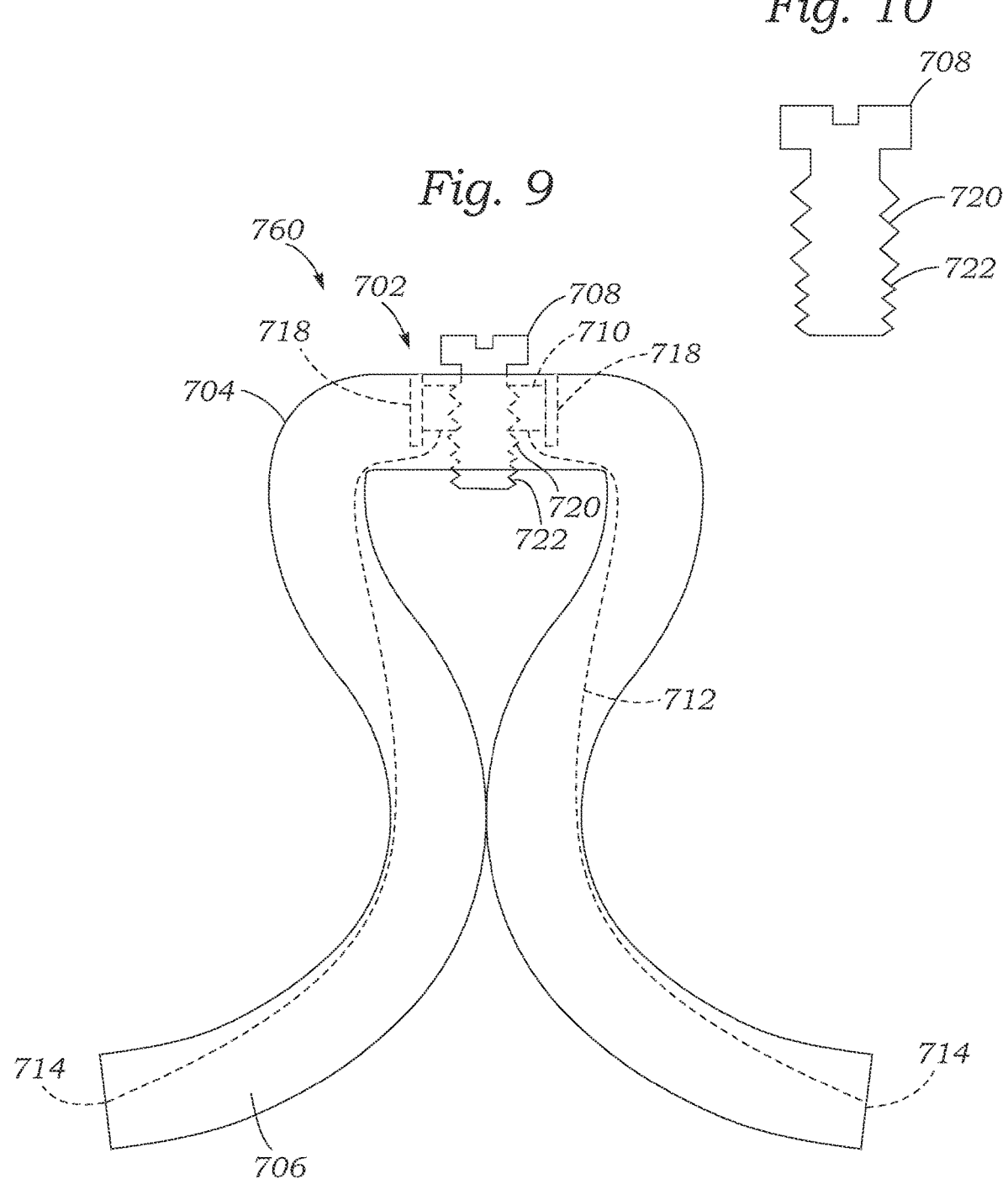
FIG. 9 is a front elevation view of another representative embodiment of a leaflet clip device.
FIG. 10 is a front elevation view of a screw of the leaflet clip device illustrated in FIG. 9.

FIG. 9 illustrates a leaflet clip device 700, according to another embodiment. The clip device 700 comprises a tensioning mechanism 702 and a clipping member 704 defining a lumen 706. The tensioning mechanism 702 can comprise a screw 708 and a nut 710 disposed on the screw, similar to the tensioning mechanism 14 of FIG. 1. Instead of a separate housing for the tensioning mechanism, the screw 708 can be at least partially disposed within the lumen 706 of the clipping member. Two walls or projections 718 can be located on opposite sides of the nut 710 within the lumen 706 to contact and prevent rotation of the nut 710 upon rotation of the screw 708.

One or more cords 712 can be disposed within the lumen 706 and can be attached at their distal end portions 714 to respective locations on the clipping member 704, as described above. The cords 712 can be attached at their proximal end portions to the nut 710. As such, rotation of the screw 708 is effective to move the nut 710 axially along the screw to adjust the tension on the cords, as described in detail above in connection with the embodiment of FIG. 1.

The tensioning mechanism 702 can include a retaining or locking mechanism in the form of a variable-pitch screw. As best shown in FIG. 10, for example, the screw 708 can include a first threaded portion 720 having threads defining a first pitch and a second threaded portion 722 having threads defining a second pitch, smaller than the first pitch. The nut 710 has internal threads that correspond to the threads of the first threaded portion 720 and can move axially along the screw upon rotation of the screw. The internal threads of the nut 710 are substantially different from the threads of the second threaded portion 722 (e.g., the threads are larger and/or have a smaller pitch than the threads of the second threaded portion) such that when the nut 710 reaches the second threaded portion 722, a mechanical interference occurs that resists further movement of the nut to assist in retaining the clipping member in its deformed state.

Figure 11:
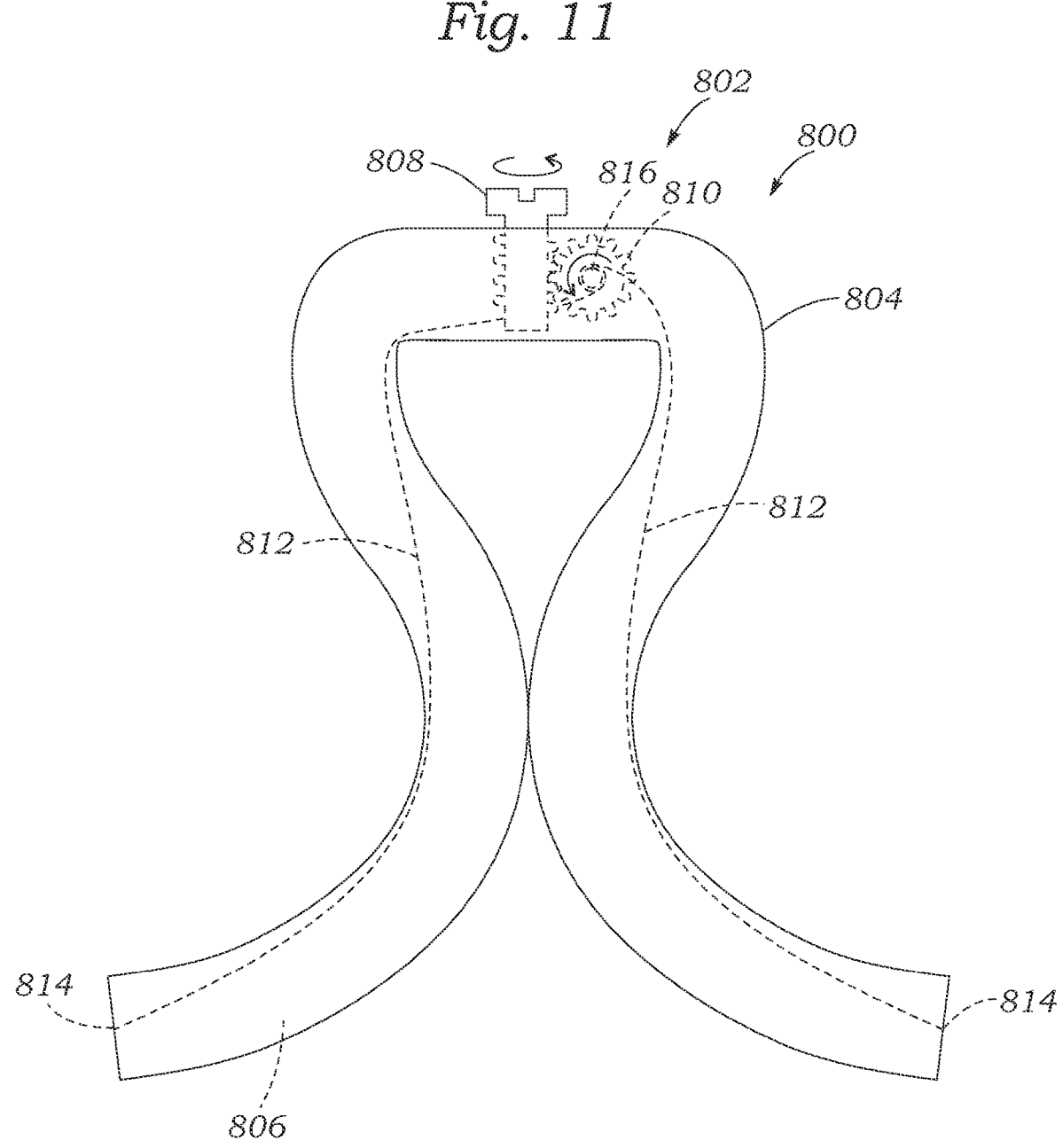
FIG. 11 is a front elevation view of another representative embodiment of a leaflet clip device.

FIG. 11 illustrates a leaflet clip device 800, according to another embodiment. The clip device 800 comprises a tensioning mechanism 802 and a clipping member 804 defining a lumen 806. The tensioning mechanism 802 can comprise a worm screw 808 and a worm wheel or gear 810 engaged with the screw 808. The screw 808 and the wheel 810 can be mounted within the lumen 806 with the proximal end portion of the screw 808 exposed outside of the clipping member for connection to a delivery apparatus or tool used for rotating the screw. Rotation or torque on the worm screw 808 is converted to rotation or torque on the worm wheel 810.

One or more cords 812 can be disposed within the lumen 806 and can be attached at their distal ends 814 to respective locations on the clipping member 804, as previously described. The one or more cords 812 can be attached at their proximal end portions to a central shaft 816 of the worm wheel 810. A mechanism in the delivery system (e.g., a torque shaft) can rotate the screw 808, causing the worm wheel 810 and the shaft 816 to rotate. As the worm wheel 810 is rotated, tension is applied to the one or more cords 812 as the slack in the cords become wrapped around the shaft 816. A single worm wheel 810 can be used to apply tension to multiple cords 812, as shown. In alternative embodiments, first and second worm wheels 810 can be mounted on respective shafts on opposite sides of the screw 808 with each wheel 810 connected to a respective cord 810 that extends through that side of the clipping member. Tension can be applied to the one or more cords 812 within the clipping member 804 until the desired predetermined implantation configuration is reached.

Figure 12:
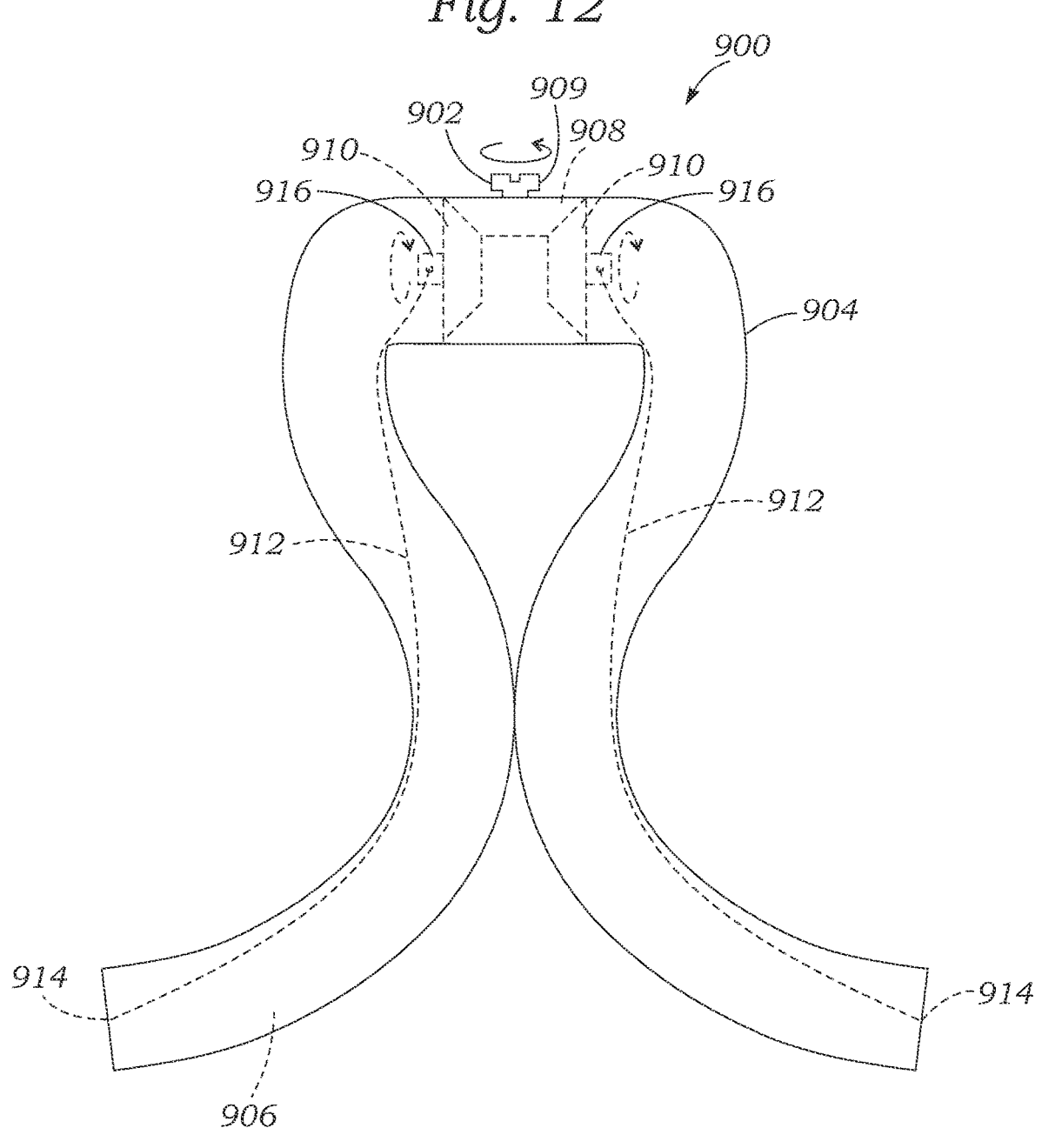
FIG. 12 is a front elevation view of another representative embodiment of a leaflet clip device.

FIG. 12 illustrates a leaflet clip device 900, according to another embodiment. The clip device 900 can comprise a tensioning mechanism 902 and a clipping member 904 defining a lumen 906. The tensioning mechanism 902 can comprise a central bevel gear 908 and one or more side bevel gears 910, for example disposed on either side of the central bevel gear 908. Each side gear 910 can be mounted on a respective shaft 916 or a common shaft that extends through both side gears 910. The gears 908, 910 can be mounted in the lumen 906 except that a shaft portion 909 of the central gear 908 can be exposed outside of the clipping member for connection to a delivery apparatus or tool used for rotating the screw. Rotation or torque of the central gear 908 (by rotating the shaft portion 909) is converted to rotation or torque on the two side gears 910.

One or more cords 912 can be disposed within the lumen 906 and can be attached at their distal end portions 914 to respective locations on the clipping member 904 as previously described. Each of the one or more cords 912 can be attached at its proximal end portion to a shaft 916 of a respective side gear 910. A mechanism in the delivery system (e.g., a torque shaft) can rotate the central gear 908, causing the side gears 910 to rotate. As the side gears 910 rotate, tension is applied to the one or more cords 912 as slack in each cord is wrapped around a respective shaft 916. Tension can be applied to the one or more cords 912 within the clipping member 904 until the desired predetermined implantation configuration is reached.

In view of the many possible embodiments to which the principles of the disclosed technology can be applied, it should be recognized that the illustrated embodiments are only preferred examples and should not be taken as limiting the scope of the disclosure. Rather, the scope of the disclosure is defined by the following claims.

What is claimed is:

1. A system comprising:
a delivery apparatus;
a leaflet clip device coupled to the delivery apparatus, the leaflet clip device comprising:
a clipping member comprising an intermediate portion, a first leg portion and a second leg portion;
a first tensioning member attached to the first leg portion;
wherein the first tensioning member is configured to apply tension to the first leg to move the first leg portion;
a second tensioning member attached to the second leg portion;
wherein the second tensioning member is configured to apply tension to the second leg portion to move the second leg portion;
wherein the clipping member can be transformed from a delivery configuration to an implantation configuration;
wherein when the clipping member is in the implantation configuration, first sections of each of the leg portions extend toward each other from respective ends of the intermediate portion of the clipping member to define a clipping region for capturing a pair of leaflets and second sections of each of the leg portions then extend away from each other moving in a direction away from the clipping region;
wherein the first tensioning member and the second tensioning member are configured to move the first leg portion and the second leg portion of the clipping member to capture one or more native valve leaflets in the implantation configuration;
wherein the delivery apparatus includes a strain gauge; and
wherein the strain gauge is configured to measure a force that can be withstood by the leaflet clip device without disengaging from the one or more native valve leaflets when the clipping member is in the implantation configuration.

2. The system of claim 1 wherein the clipping member is in a substantially longitudinally extended configuration in the delivery configuration and the first portion and the second portion are drawn toward one another as the clipping member is transformed from the delivery configuration to the implantation configuration.

3. The system of claim 1 wherein the first portion and the second portion are configured to engage a pair of the one or more native valve leaflets at a center of the native valve along coaptation edges of the pair of the one or more native valve leaflets.

4. The system of claim 1 wherein the clipping member is shape set in the implantation configuration and a resiliency of shape memory material of the clipping member provides sufficient force against a pair of the one or more native valve leaflets to anchor the clipping member onto the pair of the one or more native valve leaflets.

5. The system of claim 1 wherein the strain gauge is configured to determine a force applied by the first and second tensioning members.

6. The system of claim 5 wherein the first tensioning member comprises a first cord and the second tensioning member comprises a second cord.

7. The system of claim 1 wherein the first tensioning member comprises a first cord and the second tensioning member comprises a second cord.

8. A system comprising:

a delivery apparatus;

a leaflet clip device coupled to the delivery apparatus, the leaflet clip device comprising:

a clipping member comprising an intermediate portion, a first leg portion and a second leg portion;

wherein the clipping member can be transformed from a delivery configuration to an implantation configuration;

wherein when the clipping member is in the implantation configuration, first sections of each of the leg portions extend toward each other from respective ends of the intermediate portion of the clipping member to define a clipping region for capturing a pair of leaflets and second sections of each of the leg portions then extend away from each other moving in a direction away from the clipping region;

wherein the delivery apparatus includes a strain gauge; and wherein the strain gauge is configured to measure a force that can be withstood by the leaflet clip device without disengaging from one or more native valve leaflets when the clipping member is in the implantation configuration.

9. The system of claim 8 wherein the clipping member is in a substantially longitudinally extended configuration in the delivery configuration and the first portion and the second portion are drawn toward one another as the clipping member is transformed from the delivery configuration to the implantation configuration.

10. The system of claim 8 wherein the first portion and the second portion are configured to engage a pair of the one or more native valve leaflets at a center of the native valve along coaptation edges of the pair of the one or more native valve leaflets.

11. The system of claim 8 wherein the clipping member is shape set in the implantation configuration and a resiliency of shape memory material of the clipping member provides sufficient force against a pair of the one or more native valve leaflets to anchor the clipping member onto the pair of the one or more native valve leaflets.

12. The system of claim 8 wherein a first tensioning member comprises a first cord and a second tensioning member comprises a second cord.

16

13. A system comprising:

a delivery apparatus;

a leaflet clip device coupled to the delivery apparatus, the leaflet clip device comprising:

a clipping member comprising an intermediate portion, a first leg portion and a second leg portion;

wherein the clipping member can be transformed from a delivery configuration to an implantation configuration;

wherein when the clipping member is in the implantation configuration, first sections of each of the leg portions extend toward each other from respective ends of the intermediate portion of the clipping member to define a clipping region for capturing a pair of leaflets and second sections of each of the leg portions then extend away from each other moving in a direction away from the clipping region;

wherein the delivery apparatus includes a strain gauge; and wherein the strain gauge is configured to measure a force applied to the leaflet clip device when the clipping member is in the implantation configuration.

14. The system of claim 13 wherein the clipping member is in a substantially longitudinally extended configuration in the delivery configuration and the first portion and the second portion are drawn toward one another as the clipping member is transformed from the delivery configuration to the implantation configuration.

15. The system of claim 13 wherein the first portion and the second portion are configured to engage a pair of one or more native valve leaflets at a center of the native valve along coaptation edges of the pair of one or more native valve leaflets.

16. The system of claim 13 wherein the clipping member is shape set in the implantation configuration and a resiliency of shape memory material of the clipping member provides sufficient force against a pair of one or more native valve leaflets to anchor the clipping member onto the pair of one or more native valve leaflets.

17. The system of claim 13 wherein the strain gauge is configured to determine a force applied by first and second tensioning members.

18. The system of claim 13 wherein a first tensioning member comprises a first cord and a second tensioning member comprises a second cord.

* * * * *